(12) United States Patent
Hell et al.

(10) Patent No.: US 8,791,300 B2
(45) Date of Patent: *Jul. 29, 2014

(54) PROCESS FOR PREPARING A SUBSTITUTED DIMETHYL-(3-ARYLBUTYL)AMINE COMPOUND BY HOMOGENEOUS CATALYSIS

(75) Inventors: Wolfgang Hell, Aachen (DE); Markus Kegel, Aachen (DE); Helmut Buschmann, San Just Desvem (ES); Felix Spindler, Starrkirch-Wil (CH); Detlef Heller, Rostock (DE); Hans-Joachin Drexler, Gross-Schwass (DE)

(73) Assignee: Gruenenthal GmbH, Aachen (DE)

( * ) Notice: Subject to any disclaimer, the term of this patent is extended or adjusted under 35 U.S.C. 154(b) by 343 days.

This patent is subject to a terminal disclaimer.

(21) Appl. No.: 12/113,582

(22) Filed: May 1, 2008

(65) Prior Publication Data

US 2009/0043132 A1 Feb. 12, 2009

Related U.S. Application Data

(63) Continuation of application No. PCT/EP2006/010407, filed on Oct. 30, 2006.

(30) Foreign Application Priority Data

Nov. 2, 2005 (DE) .......................... 10 2005 052 588

(51) Int. Cl.
*C07C 211/00* (2006.01)

(52) U.S. Cl.
USPC ........................................................ 564/305

(58) Field of Classification Search
None
See application file for complete search history.

(56) References Cited

U.S. PATENT DOCUMENTS

| | | | |
|---|---|---|---|
| 4,012,456 A | 3/1977 | Chaplits | |
| 4,276,195 A | 6/1981 | Verkade | |
| 4,889,777 A | 12/1989 | Akuto | |
| 5,371,256 A | 12/1994 | Togni et al. | |
| 5,446,844 A | 8/1995 | Steckler et al. | |
| 5,583,241 A | 12/1996 | Spindler | |
| 5,811,582 A | 9/1998 | Buschmann et al. | |
| 6,203,939 B1 | 3/2001 | Wilson | |
| 6,248,737 B1 | 6/2001 | Buschmann et al. | |
| 6,372,387 B1 | 4/2002 | Kawakami et al. | |
| 7,417,170 B2 * | 8/2008 | Hell et al. | 564/358 |
| 7,589,196 B2 * | 9/2009 | Pugin et al. | 544/105 |
| 2002/0010178 A1 | 1/2002 | Buschmann et al. | |
| 2002/0074972 A1 | 6/2002 | Narang et al. | |
| 2004/0106046 A1 | 6/2004 | Inda | |
| 2004/0191630 A1 | 9/2004 | Kawamura et al. | |
| 2006/0167318 A1 | 7/2006 | Jagusch et al. | |
| 2006/0194988 A1 | 8/2006 | Hell et al. | |
| 2009/0043132 A1 | 2/2009 | Hell et al. | |
| 2010/0009916 A1 | 1/2010 | Bokvist et al. | |

FOREIGN PATENT DOCUMENTS

| | | |
|---|---|---|
| CA | 2170100 A1 | 8/1996 |
| DE | 107 260 | 7/1974 |
| DE | 124521 | 3/1977 |
| DE | 103 26 097 A1 | 1/2005 |
| DE | 103 28 316 A1 | 1/2005 |
| EP | 0 612 758 A1 | 8/1994 |
| EP | 0 646 590 A1 | 4/1995 |
| EP | 0 691 949 A1 | 1/1996 |
| EP | 0 693 475 A1 | 1/1996 |
| EP | 0 728 768 A2 | 8/1996 |
| EP | 0 729 969 A1 | 9/1996 |
| EP | 0 799 819 A1 | 10/1997 |
| GB | 1 394 542 | 5/1975 |
| JP | 6-90934 B2 | 11/1994 |
| JP | 07-326372 | 12/1995 |
| JP | 11-345629 A | 12/1999 |
| JP | 2002-158039 | 5/2002 |
| JP | 2004-185862 | 7/2004 |
| KR | 1992-0005187 B | 6/1992 |
| KR | 1999-0078427 A | 10/1999 |
| WO | WO 95/21151 A1 | 8/1995 |

(Continued)

OTHER PUBLICATIONS

U.S. Appl. No. 12/374,874, filed Jul. 2007, Hell, Wolfgang.*

(Continued)

*Primary Examiner* — Clinton Brooks

(74) *Attorney, Agent, or Firm* — Hunton & Williams LLP

(57) ABSTRACT

Compounds of the formula II (II)

can be hydrogenated to the corresponding butane derivatives in the presence of homogeneous cataslysts composed of metal salts or complexes containing metals selected from the group consisting of Rh, Ir, and Ru and preferably containing diphosphine ligands, with, in addition, excellent optical yields being achieved when one of $R^2$ and $R^3$ is not a hydrogen atom and the diphosphine ligand is chiral.

8 Claims, No Drawings

(56) References Cited

FOREIGN PATENT DOCUMENTS

| WO | WO 01/49651 A2 | 7/2001 | |
|---|---|---|---|
| WO | WO2004089920 * | 10/2004 | ........... C07D 265/36 |
| WO | WO 2004/108658 A1 | 12/2004 | |
| WO | WO 2005/000788 A1 | 1/2005 | |
| WO | WO 2007/051576 A1 | 5/2007 | |

OTHER PUBLICATIONS

David J. Ager et al. "Reductions of 1,3-dicarbonyl systems with ruthenium-biarylbisphosphine catalysts", Tetrahedron: Asymmetry Report No. 30, 1997, p. 3327-3355, vol. 8, No. 20.

John M. Brown, "Comprehensive Asymmetric Catalysis I-III: Chapter 5.1 Hydrogenation of Functionalized Carbon-Carbon Double Bonds", 1999, pp. 122-182.

Brunner et al., "Handbook of Enantioselective Catalysis with Transition Metal Compounds", vol. I: Products and Catalysts, 1993, Table of Contents (three (3) pages).

Jacobsen et al., "Comprehensive Asymmetric Catalysis I-III", 1999, Table of Contents (eight (8) pages).

Noyori, "Catalytic Asymmetric Synthesis", Second Edition, 2000, Table of Contents (five (5) pages).

T. Ohkuma et al., "Comprehensive Asymmetric Catalysis I-III: Chapter 6.1 Hydrogenation of Carbonyl Groups", 1999, pp. 199-246.

Takeshi Ohkuma et al., "Asymmetric Hydrogenation", Catalytic Asymmetric Synthesis, Second Edition, 2000, pp. 1-110.

Nadia C. Zanetti et al., "Synthesis Characterization, and Application in Asymmetric Hydrogenation Reactions of Chiral Ruthenium (II) Diphosphine Complexes", Organometallics, 1996, pp. 860-866, vol. 15.

Lubell, W. D. et al., "α-Amino Acids as Chiral Educts for Asymmetric Products. Alkylation of N-Phenylfluorenyl α-Amino Ketones. Synthesis of Optically Pure α-Alkyl Carboxylic Acids", J. Am. Chem. Soc., vol. 110, No. 22, 1988, pp. 7447-7455, XP002419870.

International Preliminary Report on Patentability including English translation (Eleven (11) pages), 2009.

Schmidle et al, J. Am. Chem. Soc., 1995, 77, 4636-4638.

Yasuda et . (J. Org. Chem, 2001 66, 7741).

Lucke et al. (English translation of DD 12451) 1977.

Tetsuji Kametani et al., "Syntheses of Analgesics. XXVIII, Syntheses of 4-Amino-3-methyl-1,2-diphenyl-2-propionyloxybutane Derivatives" Yakugaku Zhassi, vol. 92, no. 4, 1972, pp. 421-430, XP009074552, Japan p. 424.

Maurilio Tramontini, "Advances in the Chemistry of Mannich Bases", Synthesis, No. 12, 1973, XP002406126, p. 712: table 6.

International Search Report dated Oct. 30, 2007 (Seven (7) pages).

European Office Action dated Nov. 22, 2006 (Seven (7) pages).

Written Opinion of the International Search Authority (Six (6) pages), 2009.

* cited by examiner

PROCESS FOR PREPARING A SUBSTITUTED DIMETHYL-(3-ARYLBUTYL)AMINE COMPOUND BY HOMOGENEOUS CATALYSIS

CROSS REFERENCE TO RELATED APPLICATIONS

This application is a continuation of international patent application no. PCT/EP2006/010407, filed Oct. 30, 2006, designating the United States of America, and published in German on May 10, 2007 as WO 2007/051576, the entire disclosure of which is incorporated herein by reference. Priority is claimed based on Federal Republic of Germany patent application no. DE 10 2005 052 588.1, filed Nov. 2, 2005.

BACKGROUND OF THE INVENTION

The present invention relates to a process for the preparation of substituted dimethyl-(3-aryl-butyl)-amine compounds by means of homogeneous catalytic hydrogenation of dimethyl-(3-aryl-but-3-enyl)-amines.

Dimethyl-(3-aryl-butyl)-amine compounds have proved to be pharmaceutically active compounds exhibiting excellent analgesic activity and very good tolerability, see EP-A1-0 693 475. WO 2005/000788 A1 describes a process for the preparation of such compounds in which, in a first stage, substituted dimethyl-(3-aryl-but-3-enyl)-amine compounds are prepared by elimination of the tertiary hydroxyl group in substituted 4-dimethylamino-2-aryl-butan-2-ol compounds. These dimethyl-(3-aryl-but-3-enyl)-amine compounds are then hydrogenated in a second stage in the presence of metal catalysts. The heterogeneous hydrogenation proceeds in good yields with adequate activities. As expected, the stereoselectivity is not very pronounced. According to the examples in WO 2005/000788 A1, if two adjacent asymmetric C atoms are present diastereomeric ratios of from 2:1 to a maximum of 3:1 can be obtained for the trans diastereomer: cis diastereomer, that is to say always in favor of the trans diastereomer. The ratio is established automatically, essentially depends on the substrate, and can be influenced by the choice of reaction conditions to only a small extent.

SUMMARY OF THE INVENTION

The object of the present invention is to provide an improved and more flexible process for the preparation of substituted dimethyl-(3-aryl-butyl)-amine compounds. It has now been found that dimethyl-(3-aryl-but-3-enyl)-amine compounds can also be hydrogenated in a homogeneous phase in the presence of soluble hydrogenation catalysts, and high conversions and yields can be achieved by this procedure. It has furthermore been found that the stereoselectivity can be influenced in a targeted manner by the choice of chiral ligands, and very high optical yields can be achieved. It has also been found that the desired configuration can be obtained by the choice of ligands if the same substituted dimethyl-(3-aryl-but-3-enyl)-amine is used as the starting compound.

The present invention comprises a process for the preparation of a substituted dimethyl-(3-aryl-butyl)-amine compound of formula III

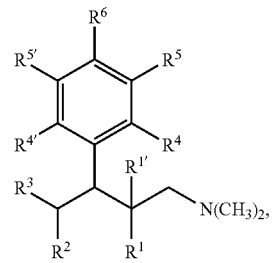

(III)

wherein
$R^1$, $R^{1'}$, $R^2$. $R^3$ each independently denote —H or —$C_{1-5}$-alkyl,
$R^4$, $R^{4'}$, $R^5$, $R^{5'}$, $R^6$ are identical or different and each represent —H, —OH, —$C_{1-4}$-alkyl, —O—$C_{1-4}$-alkyl, partly fluorinated or perfluorinated —$C_{1-4}$-alkyl, partly fluorinated or perfluorinated —O—$C_{1-4}$-alkyl, —O—$(CH_2)_n$-phenyl where n is 1, 2 or 3, F, Cl or $OR^8$, or two adjacent radicals $R^4$ and $R^5$, $R^5$ and $R^6$, $R^6$ and $R^{5'}$ or $R^{5'}$ and $R^{4'}$ represent a group —OCH=CHO—, —CH=C($R^9$)—O—, —CH=C($R^9$)—S— or —CH=CH—C($OR^{10}$)=CH— as part of a ring, with the proviso that the other particular radicals $R^6$, $R^5$ and $R^{4'}$, $R^4$, $R^{5'}$ and $R^{6'}$, $R^4$, $R^5$ and $R^{4'}$ or $R^4$, $R^5$ and $R^6$ have the abovementioned meaning,
$R^8$ denotes —CO—$C_{1-5}$-alkyl, —PO(O—$C_{1-4}$-alkyl)$_2$, —CO—$C_6H_4$—$R^{11}$, —CO(O—$C_{1-5}$-alkyl), —CO—CHR$^{12}$—NHR$^{13}$, —CO—NH—$C_6H_3$—$(R^{14})_2$ or an unsubstituted or substituted pyridyl, thienyl, thiazolyl or phenyl group,
$R^9$ denotes —H or —$C_{1-4}$-alkyl,
$R^{10}$ denotes —H or —$C_{1-3}$-alkyl,
$R^{11}$ denotes —OC(O)—$C_{1-3}$-alkyl in the ortho-position or —$CH_2$—N—$(R^{15})_2$ in the meta- or para-position, wherein $R^{15}$ in each case denotes —$C_{1-4}$-alkyl or the two radicals $R^{15}$ together with the bridging nitrogen atom form a 4-morpholino radical,
$R^{12}$ and $R^{13}$ are identical or different and each represent —H, —$C_{1-6}$-alkyl or —$C_{3-8}$-cycloalkyl, or
$R^{12}$ and $R^{13}$ together denote —$(CH_2)_{3-8}$ as part of a ring,
$R^{14}$ denotes —H, —OH, —$C_{1-7}$-alkyl, partly fluorinated or perfluorinated —$C_{1-7}$-alkyl, —$OC_{1-7}$-alkyl, -phenyl, —O-aryl, —F or —Cl, with the proviso that the radicals $R^{14}$ are identical or different,
in each case in the form of one of their pure stereoisomers, in particular enantiomers or diastereomers, their racemates or in the form of a mixture of stereoisomers, in particular the enantiomers or diastereomers, in any desired mixing ratio, optionally in the form of a salt, a solvate or in the form of a salt and solvate, which is characterized in that a substituted dimethyl-(3-aryl-but-3-enyl)-amine compound of formula II

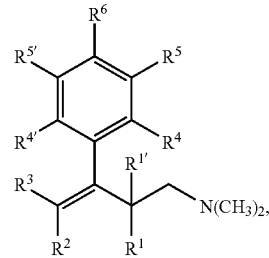

(II)

wherein $R^1$, $R^{1'}$, $R^2$, $R^3$, $R^4$, $R^{4'}$, $R^5$, $R^{5'}$ and $R^6$ each have the abovementioned meanings, in each case in the form of racemates, pure enantiomers, mixtures of enantiomers in any desired mixing ratio, Z or E isomers or mixtures of Z or E isomers in any desired mixing ratio, salts or solvates, is reacted in the presence of hydrogen and a soluble metal salt or metal complex of metals from the group of iridium, rhodium and ruthenium, as a homogeneous catalyst, to give a compound of formula III. The process according to the invention is particularly suitable for asymmetric hydrogenations if the metal salts or metal complexes contain chiral ligands.

Substituted dimethyl-(3-aryl-but-3-enyl)-amine compounds which are preferably used in the process according to the invention are those of formula IIA

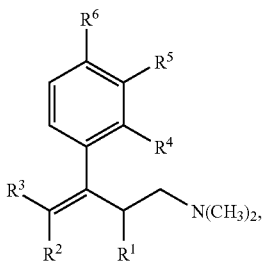

(IIA)

wherein $R^1$ is —$C_{1-5}$-alkyl, $R^2$ denotes —H or —$C_{1-5}$-alkyl, $R^3$ denotes —H or —$C_{1-5}$-alkyl, $R^4$ is —H, —OH, —$C_{1-4}$-alkyl, —O—$C_{1-4}$-alkyl, —O-benzyl, —$CF_3$, —O—$CF_3$, —Cl, —F or —$OR^8$, $R^5$ is —H, —OH, —$C_{1-4}$-alkyl, —O—$C_{1-4}$-alkyl, —O-benzyl, —$CHF_2$, —$CF_3$, —O—$CF_3$, —Cl, —F or —$OR^8$, $R^6$ denotes —H, —OH, —$C_{1-4}$-alkyl, —O—$C_{1-4}$-alkyl, —O-benzyl, —$CF_3$, —O—$CF_3$, —Cl, —F or —$OR^8$, with the proviso that two of $R^4$, $R^5$ or $R^6$ are —H, or $R^4$ and $R^5$ together denote a group —CH=C($R^9$)—O— or —CH=C($R^9$)—S— as part of a ring, wherein $R^6$ is —H, or $R^5$ and $R^6$ together denote a group —CH=CH—C($OR^{10}$)=CH— as part of a ring, wherein $R^4$ is —H, $R^8$ denotes —CO—$C_{1-5}$-alkyl, —PO(O—$C_{1-4}$-alkyl)$_2$, —CO—$C_6H_4$—$R^{11}$, —CO(O—$C_{1-5}$-alkyl), —CO—$CHR^{12}$—$NHR^{13}$, —CO—NH—$C_6H_3$—($R^{14}$)$_2$ or an unsubstituted or substituted pyridyl, thienyl, thiazolyl or phenyl group, $R^9$ denotes —H or —$C_{1-4}$-alkyl, $R^{10}$ denotes —H or $C_{1-3}$-alkyl, $R^{11}$ denotes —OC(O)—$C_{1-3}$-alkyl in the ortho-position or —$CH_2$—N—($R^{15}$)$_2$ in the meta- or para-position, wherein $R^{15}$ is —$C_{1-4}$-alkyl or the two radicals $R^{15}$ together with the bridging nitrogen atom form a 4-morpholino radical, $R^{12}$ and $R^{13}$ are identical or different and each represent —H, —$C_{1-6}$-alkyl or —$C_{3-8}$-cycloalkyl, or $R^{12}$ and $R^{13}$ together denote —$(CH_2)_{3-8}$ as part of a ring, and $R^{14}$ denotes —H, —OH, —$C_{1-7}$-alkyl, —O—$C_{1-7}$-alkyl, -phenyl, —O-aryl, —$CF_3$, —Cl or —F, with the proviso that the two radicals $R^{14}$ are identical or different.

Substituted dimethyl-(3-aryl-but-3-enyl)-amine compounds which are particularly preferably used in the process according to the invention are those of formula IIA in which $R^1$ denotes —$C_{1-3}$-alkyl, $R^2$ denotes —H or $C_{1-3}$-alkyl, $R^3$ denotes —H or $C_{1-3}$-alkyl, $R^4$ denotes —H, —OH, —Cl, —F or —$OR^8$, $R^5$ denotes —H, —OH, —$C_{1-4}$-alkyl, —O—$C_{1-4}$-alkyl, —O-benzyl, —$CHF_2$, —$CF_3$, —Cl, —F or —$OR^8$, $R^6$ denotes —H, —OH, —O—$C_{1-4}$-alkyl, —O-benzyl, —$CF_3$, —Cl, —F or —$OR^8$, with the proviso that two of $R^4$, $R^5$ or $R^6$ are —H, or $R^4$ and $R^5$ together denote a group —CH=C($R^9$)—O— or —CH=C($R^9$)—S— as part of a ring, with the proviso that $R^6$ is —H, or $R^5$ and $R^6$ together denote a group —CH=CH—C($OR^{10}$)=CH— as part of a ring, with the proviso that $R^4$ is —H, and $R^8$ to $R^{10}$ have the abovementioned meaning.

Substituted dimethyl-(3-aryl-but-3-enyl)-amine compounds which are very particularly preferably employed in the process according to the invention are those of formula IIA in which $R^1$ is —$CH_3$ or —$C_3H_7$, $R^2$ is —H, —$CH_3$ or —$CH_2CH_3$, $R^3$ is —H, —$CH_3$ or —$CH_2CH_3$, $R^4$ is —H or —OH, $R^5$ is —H, —OH, —$OCH_3$, —$CHF_2$ or —$OR^8$, $R^6$ is —H, —OH or —$CF_3$, with the proviso that two radicals $R^4$, $R^5$ or $R^6$ are —H, or $R^4$ and $R^5$ together represent a group —CH=C($CH_3$)—S— as part of a ring, wherein $R^6$ is —H, or $R^5$ and $R^6$ together denote —CH=CH—C(OH)=CH— as part of a ring, wherein $R^4$ is —H, $R^8$ denotes —CO—$C_6H_4$—$R^{11}$, and $R^{11}$ denotes —OC(O)—$C_{1-3}$-alkyl in the ortho-position.

Substituted dimethyl-(3-aryl-but-3-enyl)-amine compounds which are very particularly preferably employed in the process according to the invention are those of formula IIA in which $R^1$ and $R^3$ each represent —$CH_3$ and $R^5$ represents —$OCH_3$ and the other radicals represent a hydrogen atom, corresponding to the following formula IIB, or the 2R enantiomer of the formula IIC

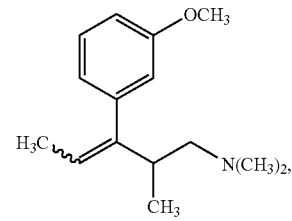

(IIB)

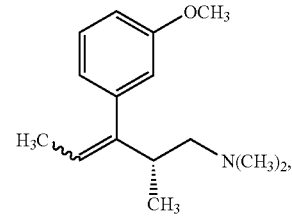

(IIC)

The compound of formula IIC, that is to say 3-[(3-methoxyphenyl)-2-methyl-pent-3-enyl]-dimethylamine, in the form of its cis or trans isomer, namely (E)-(2R)-3-[(3-methoxyphenyl)-2-methyl-pent-3-enyl]-dimethylamine according to the formula IIC.2, and particularly preferably as (Z)-(2R)-3-[(3-methoxy-phenyl)-2-methyl-pent-3-enyl]-dimethylamine according to the formula IIC.1, or mixtures with a predominant content of the Z isomer, is most preferably employed.

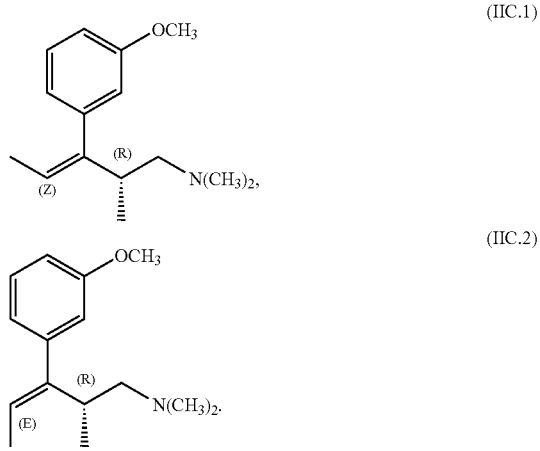

Starting from mixtures, but preferably from one of the isolated enantiomers, the largely stereoselective preparation of one of the two diastereomers of the formulae III.C1 or III.C2 is possible with the process according to the invention with the choice of appropriately suitable chiral ligands for the homogeneous catalyst:

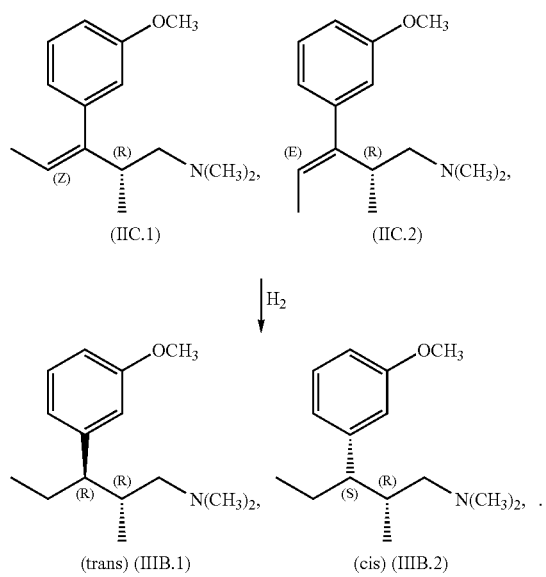

Therefore, in the process according to the invention:
(Z)-(2R)-3-[(3-methoxy-phenyl)-2-methyl-pent-3-enyl]-dimethylamine according to the formula IIB.1 is preferably employed, and
predominantly the diastereomer (2R,3R)-[3-(3-methoxy-phenyl)-2-methyl-pentyl]-dimethyl-amine of the formula IIIB.1 is preferably prepared.

The former means that the mixture of the precursors is worked up in accordance with methods known to the person skilled in the art—described briefly in the following—in order to provide the Z isomer for the hydrogenation.

The latter means that by appropriate choice of the chiral catalyst, predominantly the diastereomer (2R,3R)-[3-(3-methoxy-phenyl)-2-methyl-pentyl]-dimethyl-amine, that is to say the trans form, is obtained.

A high degree of stereoselectivity can be defined as meaning that the hydrogenation gives a product with an enantiomeric excess (abbreviated to "ee") or diastereomeric ratio (abbreviated to "d.r."). The enantiomeric excess is defined as the ratio (% R−% S)/(% R+% S), wherein % R represents the percentage content of the R form and % S represents the percentage content of the S form on a chirality centre. Since the compounds of the formulae IIB.1 and IIB.2 have the R form on the C2 atoms, after the hydrogenation the now chiral centre on the C3 atom can be present either likewise in the R or S form. Two diastereomers can therefore be present, namely the (2R,3R) or trans form and the (2R,3S) or cis form. The trans or cis form is as a rule referred to in the following for simplification, the particular diastereomers previously referred to then being meant.

With the process according to the invention, the hydrogenation can be carried out starting from a mixture of compounds of the formulae IIC.1 and IIC.2, and nevertheless a diastereomeric excess of either the trans or the cis form is obtained. For process optimization reasons, however, it is advantageous to use either the isolated Z or the isolated E isomer as the starting substance, since isolation of one of the isomers additionally renders possible the removal of by-products.

In the context of the present invention, the Z isomer is preferably used as the starting educt. By choice of an appropriate catalyst, starting from the Z isomer a ratio optionally selectively in favor of the cis or of the trans form of the product can be achieved. In this context, a ratio of greater than or equal to 70:30, preferably greater than or equal to 75:25, particularly preferably greater than or equal to 80:20, especially preferably greater than or equal to 85:15, very particularly preferably greater than or equal to 90:10, in favour of the desired cis or trans form is defined as good selectivity.

The starting compounds for the process according to the invention in the form of the substituted dimethyl-(3-aryl-but-3-enyl)-amine compounds of formulae II, IIA, IIB and IIC can be obtained e.g. by dehydration from substituted 4-dimethylamino-2-aryl-butan-2-ol compounds of formula I

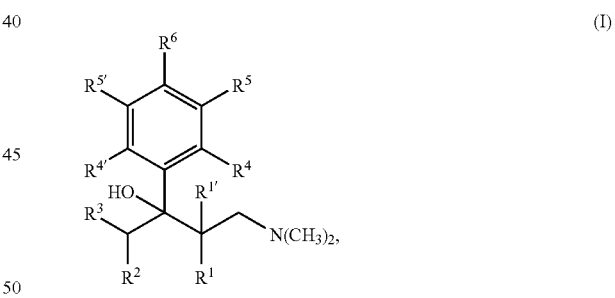

The dehydration can be carried out by means of acids, or preferably also in accordance with the process such as is described in WO 2005/000788 A1. The substituted dimethyl-(3-aryl-but-3-enyl)-amine compounds of formulae II, IIA, IIB and IIC can be in the form of a mixture of their stereoisomers. These can be separated from one another by conventional methods known to the person skilled in the art.

The reaction of the substituted dimethyl-(3-aryl-but-3-enyl)-amine compounds of formulae II, IIA, IIB and IIC to give substituted dimethyl-(3-aryl-butyl)-amine compounds of formula III optionally likewise leads to a mixture of different stereoisomers, which can be separated from one another by conventional methods known to the person skilled in the art. There may be mentioned by way of example chromatography separation methods, in particular liquid chromatography methods under normal pressure or increased pressure, preferably MPLC and HPLC methods, and methods of fractional crystallization. In this context, in particular individual enantiomers, e.g. diastereomeric salts formed by means of HPLC on a chiral phase or by means of crystallization with chiral acids, for example (+)-tartaric acid, (−)-tartaric acid or (+)-10-camphorsulfonic acid, can be separated from one another.

The substituted dimethyl-(3-aryl-but-3-enyl)-amine compounds of formulas II, IIA and IIB can be employed in the process according to the invention in each case both in the form of their bases, their acids, and in each case in the form of their salts or in each case in the form of corresponding solvates, preferably hydrates. Mixtures of two or more of the abovementioned compounds can, of course, also be employed.

If a substituted dimethyl-(3-aryl-but-3-enyl)-amine compound of formulae II, IIA, IIB and IIC in the form of a salt is reacted by the process according to the invention, this can preferably be selected from the group consisting of chloride, bromide, sulfate, sulfonate, phosphate, tartrate, embonate, formate, acetate, propionate, benzoate, oxalate, succinate, citrate, glutamate, fumarate, aspartate, glutarate, stearate, butyrate, malonate, lactate, mesylate, saccharinate, cyclamate, and particularly preferably from the group of chloride, sulfate, saccharinate, teoclate and embonate. In this context, the salts are conventionally in the form of a corresponding acid addition salt, e.g. as the hydrochloride.

If the substituted dimethyl-(3-aryl-but-3-enyl)-amine compounds of formulae II, IIA, IIB and IIC or the substituted dimethyl-(3-aryl-butyl)-amine compounds of formula III are obtained in the form of their bases by the process according to the invention, they can be converted into the corresponding salts, preferably into one of the salts listed above, by conventional processes known to the person skilled in the art.

Metal complexes of rhodium, iridium and ruthenium, preferably of rhodium and iridium, in particular of rhodium, with diphosphine ligands are particularly suitable for the process according to the invention of hydrogenation of the compounds of formulae II, IIA, IIB and IIC described above with hydrogen by means of homogeneous catalysis.

Little is known of the homogeneous catalysis of homoallylic amines of formula II. It is all the more surprising that excellent conversions and yields and very high optical yields of desired stereoisomers can be achieved, in particular when rhodium complexes are used. It may be advantageous to start from stereochemically pure educts of high chemical purity for this. However, mixtures which have not been worked up and in which Z and E isomers equally exist can optionally also be employed.

Possible diphosphine ligands include, for example, diphosphines and analogues such as are to be found, for example, in current overviews, inter alia in a) H. Brunner, W. Zettlmeier, *Handbook of Enantioselective Catalysis*. VCH Weinheim, 1993, vol. 2, page 3 et seq.; b) R. Noyori, et al. in *Catalytic Asymmetric Synthesis Second Edition* (I. Ojima, Ed.), Wiley-VCH, Weinheim, 2000, page 1 et seq.; c) E. N. Jacobsen, A. Pfaltz, H. Yamamoto (Eds.), Comprehensive *Asymmetric Catalysis vol*. I-III, Springer Berlin, 1999, and references cited therein.

Achiral and chiral structures of the secondary phosphine-skeleton-secondary phosphine type are generally possible. The two secondary phosphine groups are preferably bonded to a skeleton such that, together with the metal atom, a 5- to 10-membered, and more preferably 5- to 8-membered ring is formed in the metal complex. The two secondary phosphine groups are bonded terminally to the C atoms of a $C_2$-$C_8$-, preferably $C_2$-$C_6$- and particularly preferably $C_2$-$C_4$-chain, wherein C atoms of the chain can be replaced by hetero atoms O, S, NH and/or N—$C_1$-$C_4$-alkyl and the carbon chain can be part of a monocyclic or polycyclic ring. The skeleton can contain 2 to 30, preferably two to 20 C atoms and optionally additionally 2 to 4 hetero atoms. The skeleton can be unsubstituted or substituted, for example by $C_1$-$C_6$-alkyl, $C_1$-$C_6$-alkoxy, $C_1$-$C_6$-alkylthio, $C_4$-$C_8$-cycloalkyl, phenyl, benzyl, phenoxy, benzyloxy, phenylthio, benzylthio, halogen (preferably F, Cl, Br), OH, tri($C_1$-$C_6$-alkyl)silyl, secondary amino, —$CO_2H$, —$SO_3H$, —$CO_2R'$, —$SO_3R'$, —O—C(O)—R', —NH—C(O)R', —O—$SO_3$—R', and —NH—$SO_3R'$, wherein R' represents $C_1$-$C_6$-alkyl, $C_4$-$C_8$-cycloalkyl, phenyl or benzyl. The skeleton can be bivalent radicals of alkanes, heteroalkanes, alkenes, cycloalkanes, cycloalkenes, heterocycloalkanes, heterocycloalkenes, bicycloalkanes, bicycloheteroalkanes, spirobiscycloalkanes, spirobiscycloheteroalkanes, arylenes, heteroarylenes, bisarylenes, bisheteroarylenes, metallocenes, such as, for example, ferrocenes, wherein one or both phosphine groups can be bonded to the cyclopentadienyl ring of a metallocene via a methylene, $C_1$-$C_{12}$-alkylidene, phenylene or —CR"R*-phenylene. R" and R* independently of one another are, for example, $C_1$-$C_6$-alkyl, $C_1$-$C_6$-alkoxy or phenyl. The free bonds are on one or both cyclopentadienyl rings. In the cyclic skeletons, the free bonds are preferably in 1,2-positions and in 1,1'-bisaryls in the 6,6'-position. The secondary phosphine groups can also be bonded to C atoms of the skeleton via an oxygen atom (these are then phosphinites).

The chirality of the diphosphine ligands can be based on planar isomerism (ferrocenes), atropisomerism, the presence of asymmetric C atoms and/or P atoms or combinations thereof.

Examples of skeletons of atropisomers are 1,1'-bisaryls and -bisheteroaryls (bisaryls such as, for example, biphenyl, binaphthyl or bisthiophenyl) with secondary phosphine groups bonded in the 2,2'-positions and optionally further substituents, in particular in the 6- or in the 6,6'-positions. Trivial names for such ligands are Binap, Biphemp, Biphep and Solphos. Bicyclopentanes, which are commercially obtainable under the trivial name Bicp, are also known as the base skeleton.

Examples of skeletons having planar chirality are those based on ferrocenes with two secondary phosphine groups bonded directly to in each case one of the cyclopentadienyl rings or bonded to a cyclopentadienyl ring in the 1,2-position and optionally chiral substituents on one or both cyclopentadienyl rings. Another example are ferrocenes to which a secondary phosphine group is bonded in the 1,2-position of the cyclopentadienyl ring and a further secondary phosphine group is bonded via an asymmetric C atom. A further example are ferrocenes to which a secondary phosphine group is bonded in the 1,2-position of the cyclopentadienyl ring via an asymmetric C atom and a second secondary phosphine group is bonded via 1,2-phenylene. Trivial names for such ligands are Josiphos, Walphos, Taniaphos, Mandyphos and Ferriphos.

Diphosphines having chiral P rings which are substituted in particular in one or both α-positions to the P atom, for example phospholanes and phosphetanes, are also known. Such secondary phosphine groups can be bonded in the 1,2-position of benzene, naphthalene, thiophene, benzothiophene, ethane and ferrocene. Known trivial names are Rophos, Butiphane and Kephos.

Examples of skeletons having asymmetric carbon atoms are open-chain with in the 1,2-, 1,3- or 1,4-positions, aliphatic bicyclic ring systems with secondary phosphine groups bonded in the 1,2-positions, or cyclic or heterocyclic five-membered rings with secondary phosphine groups bonded in the 3,4-positions, optionally via a methylene group. Five-membered rings with a secondary phosphine group bonded in the 4-position and a secondary phosphinemethyl group bonded in the 2-position are also known. Trivial names for such ligands are Diop, Bppm, Bzppm, Depyphos, Norphos and Prophos.

Examples of diphosphines having chiral phosphorous atoms include 1,2-bis(secondary phosphine)ethanes with different substituents in the phosphine groups. A known representative is obtainable under the trivial name Dipamp.

The secondary phosphine groups can contain identical or different hydrocarbon radicals as substituents, and the two secondary phosphine groups in the diphosphines can be identical or different. Good results can often be achieved if the secondary phosphine groups are not identical but are different. The hydrocarbon radicals can be unsubstituted or substituted and/or can contain hetero atoms selected from the group O, S, —N= or N($C_1$-$C_4$-alkyl). They can contain 1 to 22, preferably 1 to 12 and particularly preferably 1 to 8 C atoms.

A preferred secondary phosphine is one in which the phosphine group contains two identical or different radicals selected from the group of linear or branched $C_1$-$C_{12}$-alkyl; $C_5$-$C_{12}$-cycloalkyl or $C_6$-$C_{12}$-cycloalkyl-$CH_2$— which is unsubstituted or substituted by $C_1$-$C_6$-alkyl or $C_1$-$C_6$-alkoxy; phenyl, naphthyl, furyl or benzyl; or phenyl or benzyl which is substituted by halogen, $C_1$-$C_6$-alkyl, trifluoromethyl, $C_1$-$C_6$-alkoxy, trifluoromethoxy, $(C_6H_5)_3$Si, $(C_1$-$C_{12}$-alkyl$)_3$Si or secondary amino.

Examples of substituents on P as alkyl which preferably contains 1 to 6 carbon atoms include methyl, ethyl, n-propyl, i-propyl, n-butyl, i-butyl, t-butyl and the isomers of pentyl and hexyl. Examples of substituents on P as cycloalkyl optionally substituted by alkyl include cyclopentyl, cyclohexyl, methyl- and ethylcyclohexyl and dimethylcyclohexyl. Examples of substituents on P as phenyl and benzyl substituted by alkyl and alkoxy are methylphenyl, dimethylphenyl, trimethylphenyl, ethylphenyl, methylbenzyl, methoxyphenyl, dimethoxyphenyl, trimethoxyphenyl, trifluoromethylphenyl, bis-trifluoromethylphenyl, tris-trifluoromethylphenyl, trifluoromethoxyphenyl, bis-trifluoromethoxyphenyl, fluoro- and chlorophenyl and 3,5-dimethyl-4-methoxy-phenyl.

Preferred secondary phosphine groups are those which identical or different radicals selected from the group of $C_1$-$C_6$-alkyl, or cyclopentyl or cyclohexyl which is unsubstituted or substituted by 1 to 3 $C_1$-$C_4$-alkyl or $C_1$-$C_4$-alkoxy, or benzyl and in particular phenyl, which are unsubstituted or substituted by 1 to 3 $C_1$-$C_4$-alkyl, $C_1$-$C_4$-alkoxy, $C_1$-$C_4$-fluoroalkyl or $C_1$-$C_4$-fluoroalkoxy, F and Cl.

The secondary phosphino group preferably corresponds to the formula —$PR_{16}R_{17}$, wherein $R_{16}$ and $R_{17}$ independently of one another represent a hydrocarbon radical having 1 to 18 C atoms, which is unsubstituted or substituted by $C_1$-$C_6$-alkyl, trifluoromethyl, $C_1$-$C_6$-alkoxy, trifluoromethoxy, ($C_1$-$C_4$-alkyl$)_2$-amino, $(C_6H_5)_3$Si, $(C_1$-$C_{12}$-alkyl$)_3$Si, halogen, and/or contains hetero atoms O.

$R_{16}$ and $R_{17}$ are preferably radicals selected from the group of linear or branched $C_1$-$C_6$-alkyl, or cyclopentyl or cyclohexyl which is unsubstituted or substituted by one to three $C_1$-$C_4$-alkyl or $C_1$-$C_4$-alkoxy, furyl, benzyl which is unsubstituted or substituted by one to three $C_1$-$C_4$-alkyl or $C_1$-$C_4$-alkoxy, and in particular phenyl which is unsubstituted or substituted by one to three F, Cl, $C_1$-$C_4$-alkyl, $C_1$-$C_4$-alkoxy, $C_1$-$C_4$-fluoroalkyl or $C_1$-$C_4$-fluoroalkoxy. $R_{16}$ and $R_{17}$ particularly preferably denote radicals selected from the group of $C_1$-$C_6$-alkyl, cyclopentyl, cyclohexyl, furyl, and phenyl which is unsubstituted or substituted by one to three F, Cl, $C_1$-$C_4$-alkyl, $C_1$-$C_4$-alkoxy and/or $C_1$-$C_4$-fluoroalkyl. If $R_{16}$ and $R_{17}$ in the group —$PR_{16}R_{17}$ are different, ligands which are additionally chiral on the P are present.

The secondary phosphine group can be cyclic secondary phosphino, for example those of the formulae

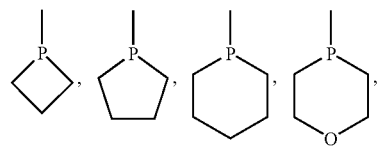

which are unsubstituted or substituted once or several times by $C_1$-$C_8$-alkyl, $C_4$-$C_8$-cycloalkyl, $C_1$-$C_6$-alkoxy, $C_1$-$C_4$-alkoxy-$C_1$-$C_4$-alkyl, phenyl, $C_1$-$C_4$-alkyl- or $C_1$-$C_4$-alkoxyphenyl, benzyl, $C_1$-$C_4$-alkyl- or $C_1$-$C_4$-alkoxybenzyl, benzyloxy, $C_1$-$C_4$-alkyl- or $C_1$-$C_4$-alkoxybenzyloxy, or $C_1$-$C_4$-alkylidene-dioxyl.

The substituents can be attached in one or both α-positions to the P atom, in order to introduce chiral carbon atoms. The substituents in one or both α-positions are preferably $C_1$-$C_4$-alkyl or benzyl, for example methyl, ethyl, n- or i-propyl, benzyl or —$CH_2$—O—$C_1$-$C_4$-alkyl or —$CH_2$—O—$C_6$-$C_{10}$-aryl.

Substituents in the β,γ-positions can be, for example, $C_1$-$C_4$-alkyl, $C_1$-$C_4$-alkoxy, benzyloxy, or —O—$CH_2$—O—, —O—CH($C_1$-$C_4$-alkyl)-O—, and —O—C($C_1$-$C_4$-alkyl$)_2$-O—. Some examples are methyl, ethyl, methoxy, ethoxy, —O—CH(methyl)-O—, and —O—C(methyl$)_2$-O—.

Depending on the nature of the substituents and the number of substituents, the cyclic phosphine radicals can be chiral at the carbon atom, chiral at the phosphorous atom or chiral at both the carbon atom and the phosphorous atom.

An aliphatic 5- or 6-membered ring or benzene can be fused to two adjacent carbon atoms in the radicals of the above formulae.

The cyclic secondary phosphino can correspond, for example, to the following formulae (only one of the possible diastereomers is shown)

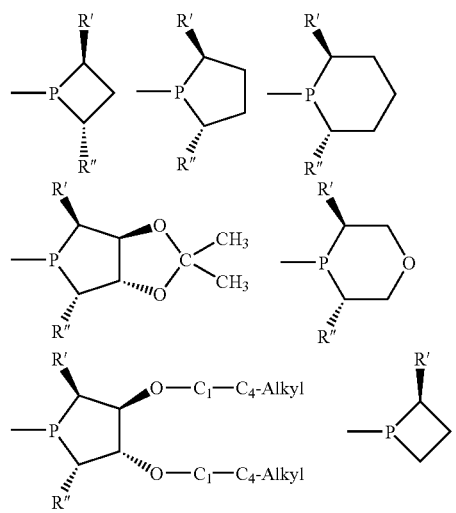

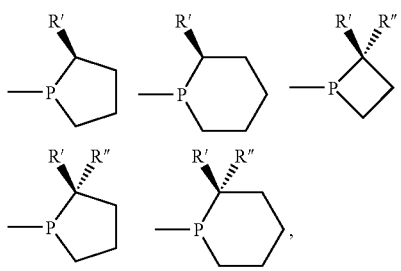

wherein

R' and R" represent $C_1$-$C_4$-alkyl, for example methyl, ethyl, n- or i-propyl, benzyl, or —$CH_2$—O—$C_1$-$C_4$-alkyl or —$CH_2$—O—$C_6$-$C_{10}$-aryl, and R' and R" are identical or different from one another.

The two secondary phosphino radicals —$PR_{16}R_{17}$ in diphosphines preferably independently of one another denote non-cyclic secondary phosphine selected from the group of —P($C_1$-$C_6$-alkyl)$_2$, —P($C_5$-$C_8$-cycloalkyl)$_2$, —P($C_7$-$C_8$-bicycloalkyl)$_2$, —P(o-furyl)$_2$, —P($C_6H_5$)$_2$, —P[2-($C_1$-$C_6$-alkyl)$C_6H_4$]$_2$, —P[3-($C_1$-$C_6$-alkyl)$C_6H_4$]$_2$, —P[4-($C_1$-$C_6$-alkyl)$C_6H_4$]$_2$, —P[2-($C_1$-$C_6$-alkoxy)$C_6H_4$]$_2$, —P[3-($C_1$-$C_6$-alkoxy)$C_6H_4$]$_2$, —P[4-($C_1$-$C_6$-alkoxy)$C_6H_4$]$_2$, —P[2-(trifluoromethyl)$C_6H_4$]$_2$, —P[3-(trifluoromethyl)$C_6H_4$]$_2$, —P[4-(trifluoromethyl)$C_6H_4$]$_2$, —P[3,5-bis(trifluoromethyl)$C_6H_3$]$_2$, —P[3,5-bis($C_1$-$C_6$-alkyl)$_2C_6H_3$]$_2$, —P[3,5-bis($C_1$-$C_6$-alkoxy)$_2C_6H_3$]$_2$, and —P[3,5-bis($C_1$-$C_6$-alkyl)$_2$-4-($C_1$-$C_6$-alkoxy)$C_6H_2$]$_2$, or cyclic phosphine selected from the group of

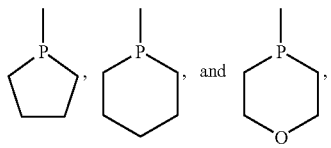

which are unsubstituted or substituted once or several times by $C_1$-$C_4$-alkyl, $C_1$-$C_4$-alkoxy, $C_1$-$C_4$-alkoxy-$C_1$-$C_2$-alkyl, phenyl, benzyl, benzyloxy, or $C_1$-$C_4$-alkylidene-dioxyl.

Some specific examples include —P($CH_3$)$_2$, —P(i-$C_3H_7$)$_2$, —P(n-$C_4H_9$)$_2$, —P(i-$C_4H_9$)$_2$, —P(t-$C_4H_9$)$_2$, —P($C_5H_9$), —P($C_6H_{11}$)$_2$, —P(norbornyl)$_2$, —P(o-furyl)$_2$, —P($C_6H_5$)$_2$, P[2-(methyl)$C_6H_4$]$_2$, —P[3-(methyl)$C_6H_4$]$_2$, —P[4-(methyl)$C_6H_4$]$_2$, —P[2-(methoxy)$C_6H_4$]$_2$, —P[3-(methoxy)$C_6H_4$]$_2$, —P[4-(methoxy)$C_6H_4$]$_2$, —P[3-(trifluoromethyl)$C_6H_4$]$_2$, —P[4-(trifluoromethyl)$C_6H_4$]$_2$, —P[3,5-bis(trifluoromethyl)$C_6H_3$]$_2$, —P[3,5-bis(methyl)$_2C_6H_3$]$_2$, —P[3,5-bis(methoxy)$_2C_6H_3$]$_2$, and —P[3,5-bis(methyl)$_2$-4-(methoxy)$C_6H_2$]$_2$, and those of the formulae

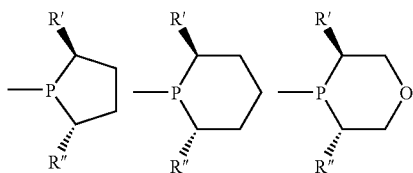

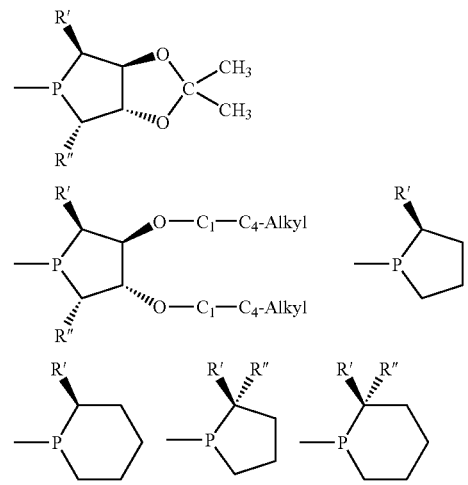

wherein

R' represents methyl, ethyl, methoxy, ethoxy, phenoxy, benzyloxy, methoxymethyl, ethoxymethyl or benzyloxymethyl and R" independently has the same meaning as R'.

Preferred diphosphine ligands are selected from those of the formulae:

(A) Ligands of formula:

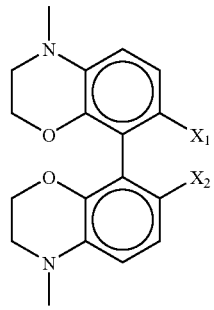

(A)

(B) Ligands of formula:

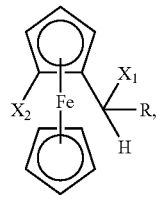

(B)

(C) Ligands of formula:

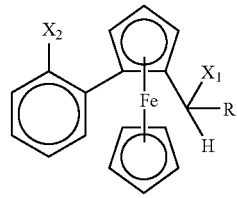

(C)

(D-G) Ligands of formulae:

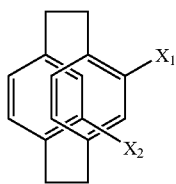
(D)

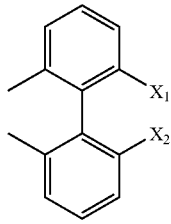
(E)

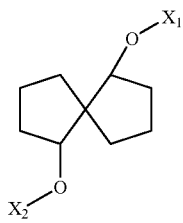
(F)

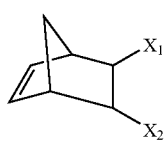
(G)

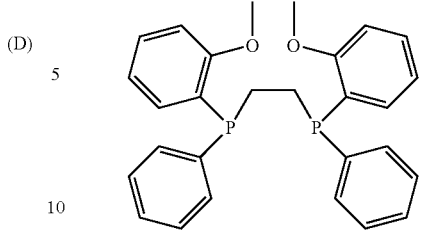
(H)

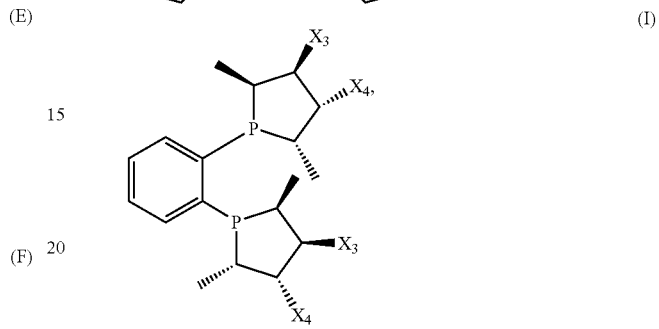
(I)

Wherein $X_3$ and $X_4$ each independently denote H, OH, $C_1$-$C_4$-alkyl, $C_1$-$C_4$-alkoxy, benzyloxy, —CH($C_1$-$C_4$-alkyl)- or —CH(phenyl)-, preferably in each case —OH.

Finally, preferred diphosphine ligands are generally those with which a diastereomeric ratio in favor of either the trans or the cis form of greater than or equal to 70:30, preferably greater than or equal to 75:25, particularly preferably greater than or equal to 80:20, especially preferably greater than or equal to 85:15, very particularly preferably greater than or equal to 90:10 can be achieved.

Very particularly preferred embodiments of the process according to the invention include:

a) A process characterized in that a compound of the formula IIC.1

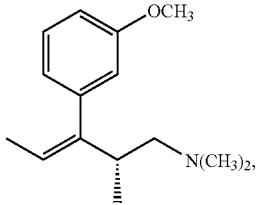
(IIC.1)

is employed, the diphosphine ligand is chosen from a compound of the formulae A to F, and the diastereomer (2R,3R)-[3-(3-methoxy-phenyl)-2-methyl-pentyl]-dimethyl-amine is predominantly obtained as the compound of the formula II, wherein the diastereomeric ratio (2R,3R):(2S,3R) is greater than or equal to 75:25.

b) A process characterized in that a compound of the formula IIC.1

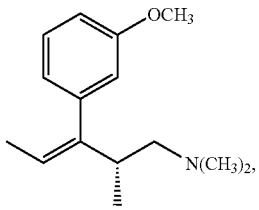
(IIC.1)

In the ligands of formulae A to G, $X_1$ and $X_2$ denote P-bonded secondary phosphine groups, including the embodiments and preferred meanings.

A very particularly preferred ligand of formula A contains as the radical $X_1$ and $X_2$ in each case an unsubstituted diphenylphosphine group.

A very particularly preferred ligand of formula B contains as the radical $X_1$ a di(2-furyl)phosphine group, as the radical $X_2$ a dixylylphosphine group, and as the radical R a methyl group.

A very particularly preferred ligand of formula C contains as the radical $X_1$ a dixylylphosphine group, as the radical $X_2$ likewise a dixylylphosphine group, and as the radical R a methyl group.

Very particularly preferred ligands of formulae D, F and G contain as the radical $X_1$ and $X_2$ in each case an unsubstituted diphenylphosphine group.

A very particularly preferred ligand of formula E contains as the radical $X_1$ a dixylylphosphine group, and as the radical $X_2$ a dicyclohexylphosphine group.

R in formulas B and C represents the possible radicals $C_1$-$C_4$-alkyl, preferably methyl, $C_6$-$C_{10}$-aryl, preferably phenyl, or $C_7$-$C_{12}$-aralkyl, preferably benzyl.

Ligands which are furthermore preferred are those of formulas H and I:

is employed, the diphosphine ligand is selected from a compound of formula G, H or I, and the diastereomer (2S,3R)-[3-(3-methoxy-phenyl)-2-methyl-pentyl]-dimethyl-amine is predominantly obtained as the compound of the formula III, wherein the diastereomeric ratio (2S,3R):(2R,3R) is greater than or equal to 75:25.

The disecondary diphosphines, including the embodiments and preferred meanings, are ligands for metal complexes of rhodium, iridium and ruthenium, preferably of rhodium and iridium, in particular of rhodium, which are outstanding catalysts or catalyst precursors for asymmetric hydrogenation of the prochiral or chiral, unsaturated organic compounds of formula II.

The metal complexes can contain further ligands and/or anions, depending on the oxidation number and coordination number of the rhodium. They can be cationic metal complexes. Such analogous metal complexes and the preparation thereof are described in many instances in the literature.

The metal complexes can correspond, for example, to formulas IV and V,

$$A_1MeL_n \quad (IV),$$

$$(A_1MeL_n)^{(z+)}(E^-)_z \quad (V),$$

wherein
$A_1$ represents a diphosphine ligand, including the embodiments and preferred meanings, in particular of the formulas A to I,
L represents identical or different monodentate, anionic or nonionic ligands, or two L represent identical or different bidentate, anionic or nonionic ligands;
n represents 2, 3 or 4 if L denotes a monodentate ligand, or n represents 1 or 2 if L denotes a bidentate ligand;
z represents 1, 2 or 3;
Me=rhodium (Rh), iridium (Ir) and ruthenium (Ru), preferably Rh and Ir, in particular Rh; wherein the metal has the oxidation levels 0, 1, 2, 3 or 4;
$E^-$ is the anion of a oxygen acid or complex acid; and
the anionic ligands compensate the charge of the oxidation levels 1, 2, 3 or 4 of the metal.

Monodentate nonionic ligands can be selected, for example, from the group of olefins (for example ethylene, propylene), allyls (allyl, 2-methallyl, solvating solvents (nitriles, linear or cyclic ethers, optionally N-alkylated amides and lactams, amines, phosphines, alcohols, carboxylic acid esters, sulfonic acid esters), nitrogen monoxide and carbon monoxide.

Monodentate anionic ligands can be selected, for example, from the group of halide (F, Cl, Br, I), pseudohalide (cyanide, cyanate, isocyanate) and anions of carboxylic acids, sulfonic acids and phosphonic acids (carbonate, formate, acetate, propionate, methylsulfonate, trifluoromethylsulfonate, phenylsulfonate, tosylate).

Bidentate nonionic ligands can be selected, for example, from the group of linear or cyclic diolefins (for example hexadiene, cyclooctadiene, norbornadiene), dinitriles (malonodinitrile), optionally N-alkylated carboxylic acid diamides, diamines, diphosphines, diols, acetonylacetonates, dicarboxylic acid diesters and disulfonic acid diesters.

Bidentate anionic ligands can be chosen, for example, from the group of anions of dicarboxylic acids, disulfonic acids and diphosphonic acids (for example of oxalic acid, malonic acid, succinic acid, maleic acid, methylenedisulfonic acid and methylenediphosphonic acid).

Preferred metal complexes are also those wherein E represents —Cl⁻, —Br⁻, —I⁻, $ClO_4^-$, $CF_3SO_3^-$, $CH_3SO_3^-$, $HSO_4^-$, $BF_4^-$, $B(phenyl)_4^-$, $B(C_6F_5)_4^-$, $B(3,5\text{-bistrifluoromethyl-phenyl})_4^-$, $PF_6^-$, $SbCl_6^-$, $AsF_6^-$ or $SbF_6^-$.

Particularly preferred metal complexes correspond to formulas VI and VII

$$[A_1Me_1YZ] \quad (VI),$$

$$[A_1Me_1Y]^+E_1^- \quad (VII),$$

wherein
$A_1$ represents a diphosphine ligand, including the embodiments and preferred meanings, in particular of the formulae A to I;
$Me_1$ denotes rhodium (Rh) and iridium (Ir), in particular Rh;
Y represents two olefins or a diene;
Z denotes Cl, Br or I; and
$E_1^-$ represents the anion of an oxygen acid or complex acid.

Y in the meaning as olefin can be $C_2$-$C_{12}$-, preferably $C_2$-$C_6$- and particularly preferably $C_2$-$C_4$-olefins. Examples are propene, but-1-ene and, in particular, ethylene. The diene can contain 5 to 12, and preferably 5 to 8 C atoms, and it can also be open-chain, cyclic or polycyclic dienes. The two olefin groups of the diene are preferably joined by one or two $CH_2$ groups. Examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Preferably, Y represents two ethylene or 1,5-hexadiene, 1,5-cyclooctadiene or norbornadiene.

In formula VI, Z preferably represents Cl or Br. Examples of $E_1$ are $ClO_4^-$, $CF_3SO_3^-$, $CH_3SO_3^-$, $HSO_4^-$, $BF_4^-$, $B(phenyl)_4^-$, $PF_6^-$, $SbCl_6^-$, $AsF_6^-$ or $SbF_6^-$.

Ruthenium complexes can correspond, for example, to the formula VIII

$$[Ru_aH_bZ_c(A_1)_dL_e](E^k)_g(S)_h \quad (VIII),$$

wherein
Z denotes Cl, Br or I;
$A_1$ represents a compound of the formulae I or Ia;
L represents identical or different ligands;
$E^-$ is the anion of an oxygen acid, mineral acid or complex acid;
S represents a solvent, as a ligand, which is capable of coordination;
a denotes 1 to 3,
b denotes 0 to 4,
c denotes 0 to 6,
d denotes 1 to 3,
e denotes 0 to 4,
f denotes 1 to 3,
g denotes 1 to 4,
h denotes 0 to 6, and
k denotes 1 to 4,
and wherein the total charge of the complex is neutral.

The preferred meanings of Z, $A_1$, L and $E^-$ described above apply to the compounds of the formula VIII. The ligands I can additionally be arenes or heteroarenes (for example benzene, naphthalene, methylbenzene, xylene, cumene, 1,3,5-mesitylene, pyridine, biphenyl, pyrrole, benzimidazole or cyclopentadienyl) and metal salts having a Lewis acid function (for example $ZnCl_2$, $AlCl_3$, $TiCl_4$ and $SnCl_4$). The solvent ligands can be, for example, alcohols, amines, acid amides, lactams and sulfones.

Complexes of this type are described in the literature mentioned in the following and in the literature cited therein:
D. J. Ager, S. A. Laneman, Tetrahedron: Asymmetry, 8, 1997, 3327-3355; T. Ohkuma, R. Noyori in Comprehensive Asymmetric Catalysis (E. N. Jacobsen, A. Pfaltz, H. Yamamoto, Eds.), Springer, Berlin, 1999, 199-246;

J. M. Brown in Comprehensive Asymmetric Catalysis (E. N. Jacobsen, A. Pfaltz, H. Yamamoto, Eds.), Springer, Berlin, 1999, 122-182;

T. Ohkuma, M. Kitamura, R. Noyori in Catalytic Asymmetric Synthesis, $2^{nd}$ Edition (I. Ojima, Ed.), Wiley-VCH New York, 2000, 1-110;

N. Zanetti, et al. Organometallics 15, 1996, 860.

The metal complexes are prepared by methods known in the literature (see e.g. Comprehensive Asymmetric Catalysis I bis III, Springer Verlag, Berlin, 1999, and literature cited therein).

The process according to the invention can be carried out under the usual conditions known in the art as suitable process parameters for hydrogenation, that is to say suitable conditions with respect to pressure, temperature, solvents and reactant amounts. The most important parameters are summarized as follows:

The process according to the invention can be carried out at low or elevated temperatures, for example temperatures of from −20 to 150° C., preferably from −10 to 100° C., and particularly preferably from 10 to 80° C. The optical yields are in general better at lower temperature that at higher temperatures.

The process according to the invention can be carried out under normal pressure or elevated pressure. The pressure can be, for example, from $10^5$ to $2 \times 10^7$ Pa (Pascal). Hydrogenations are preferably carried out under elevated pressure.

Catalysts are preferably used in amounts of from 0.00001 to 10 mol %, particularly preferably 0.0001 to 5 mol %, and especially preferably 0.001 to 2 mol %, based on the compound to be hydrogenated.

The preparation of the ligands and catalysts and the hydrogenation can be carried out without or in the presence of an inert solvent, it being possible to employ one solvent or mixtures of solvents. Suitable solvents are, for example, aliphatic, cycloaliphatic and aromatic hydrocarbons (pentane, hexane, petroleum ether, cyclohexane, methylcyclohexane, benzene, toluene, xylene), aliphatic halohydrocarbons (methylene chloride, chloroform, di- and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic acid esters and lactones (ethyl or methyl acetate, valerolactone), N-substituted lactams (N-methylpyrrolidone), carboxylic acid amides (dimethylacetamide, dimethylformamide), acyclic ureas (dimethylimidazoline), and sulfoxides and sulfones (dimethylsulfoxide, dimethyl sulfone, tetramethylene sulfoxide, tetramethylene sulfone) and alcohols (methanol, ethanol, propanol, butanol, ethylene glycol monomethyl ether, ethylene glycol monoethyl ether, diethylene glycol monomethyl ether, trifluoroethanol) and water. The solvents can be used by themselves or in a mixture of at least two solvents.

It may be advantageous to carry out the reaction in the presence of metal or ammonium halides which are soluble in the reaction mixture, for example alkali metal chlorides, bromides and iodides, or quaternary ammonium halides, such as, for example, tetrabutylammonium iodide.

It may be particularly expedient, for example if the substrate is employed as a free base, to carry out the hydrogenation in the presence of acids, for example organic acids, such as sulfonic acids (methanesulfonic acid, trifluoromethanesulfonic acid), carboxylic acids (formic acid, acetic acid, oxalic acid), phosphonic acids (methanephosphonic acid), mineral acids, such as hydrogen halide acids (HCl, HBr, HI), sulfuric acid, phosphorous acid, phosphoric acid (see, for example, U.S. Pat. Nos. 5,371,256, 5,446,844 and 5,583,241 and EP-A-0 691 949). The acid can be chosen such that a desired salt of the active compound is obtained directly. The amount of acid can accordingly be up to 1 equivalent or more, for example an excess of up to 1.5 equivalents, based on the amount of substrate to be hydrogenated. A suitable range of amounts is 0.01 to 1 equivalent of acid, based on the amount of substrate to be hydrogenated.

The metal complexes used as catalysts can be added as separately prepared, isolated compounds, or can preferably also be formed in situ before the reaction and then mixed with the substrate to be hydrogenated. It may be advantageous additionally to add ligands in the reaction using isolated metal complexes, or to employ an excess of the ligands in the in situ preparation. The excess can be, for example, 1 to 10, and preferably 1 to 5 mol percent, based on the metal compound used for the preparation.

The process according to the invention is in general carried out by a procedure in which the catalyst is initially introduced into the reaction vessel and the substrate, optionally reaction auxiliaries and the gaseous compound to be added on, in the form of hydrogen, are preferably forced in. The process can be carried out continuously or batchwise in various types of reactor.

The chiral organic compounds which can be prepared according to the invention are active substance or intermediate products for the preparation of such substances, in particular in the field of preparation of pharmaceuticals.

The following examples illustrate the invention.

Gas Chromatography (GC) Determinations are Carried Out as Follows:

a) Sample preparation: tert-Butyl methyl ether is added to the sample material. Hydrochlorides are liberated with Dowex MWA-1 to give the base. The clear organic phase is injected.

b) Gas chromatography conditions: Capillary column: 6% cyanopropyl-phenyl, 94% dimethylpolysiloxane, e.g. Optima 1301-DF 30 m×0.32 mm, 1.0 μm film thickness; carrier gas: helium; pre-pressure: 70 kPa; split: 20 ml/min; oven temperature programme: initial 160° C./5 min, rate 5° C./min, 190° C./9 min, rate 10° C./min; 250° C./14 min; detector temperature: FID/260° C.

A) Preparation of Starting Compounds [Compounds of Formula (II)]:

EXAMPLE A1

(Z,E)-(2R)-[3-(3-Methoxy-phenyl)-2-methyl-pent-3-enyl]-dimethyl-amine 28.7 g (0.1 mol) of (2S,3R)-1-dimethylamino-3-(3-methoxy-phenyl)-2-methyl-pentan-3-ol hydrochloride are initially introduced into a 250 ml three-necked flask with a thermometer, mechanical compressed air stirrer, reflux condenser and oil bath heating and 150 ml of aqueous 36 wt. % strength hydrochloric acid are added. The mixture is heated to 100° C. for 1 h. It is cooled to 20° C. and adjusted to a pH of 11 with 33 wt. % strength sodium hydroxide solution at 20° C., while cooling. 150 ml of ethyl acetate are added, the mixture is stirred for 10 min, the stirrer is switched off, the phases are separated and the ethyl acetate is distilled off on a rotary evaporator at 60° C. down to a pressure of 10 mbar. The oily residue consists of (Z,E)-(2R)-[3-(3-methoxy-phenyl)-2-methyl-pent-3-enyl]-dimethyl-amine with a GC purity of 86%, a Z/E ratio of 6.5:1 and a yield of 21 g (90% of theory). In the purity analysis, no starting product and 8.5% of (Z,E)-[3-(3-methoxy-phenyl)-2-methyl-pent-2-enyl]-dimethyl-amine was found.

EXAMPLE A2

(Z)-(2R)-[3-(3-Methoxy-phenyl)-2-methyl-pent-3-enyl]-dimethyl-amine 201 g (0.86 mol) of a mixture of (Z)-(2R)-[3-(3-methoxy-phenyl)-2-methyl-pent-3-enyl]-dimethyl-amine, (E)-(2R)-[3-(3-methoxy-phenyl)-2-methyl-pent-3-enyl]-dimethyl-amine and by-products (see Example 1) are dissolved in 1 l of acetone and 15.5 g (0.86 mol) of water are added. 94.0 g (0.87 mol) of trimethylchlorosilane are then added dropwise and the mixture is stirred at 5° C.-8° C. for 72 h. The crystals which have precipitated out are filtered off with suction and rinsed with acetone. The product is then dried in a drying cabinet under 80-120 mbar at 40-50° C. The (Z)-(2R)-[3-(3-methoxy-phenyl)-2-methyl-pent-3-enyl]-dimethyl-amine hydrochloride crude product obtained is dissolved in 513 ml of water and the solution is adjusted to a pH of 11-12 with sodium hydroxide solution. 500 ml of ethyl acetate are added to the aqueous solution and the product is extracted. The ethyl ester phase which has been separated off is dried over sodium sulfate and concentrated on a rotary evaporator. The (Z)-(2R)-[3-(3-methoxy-phenyl)-2-methyl-pent-3-enyl]-dimethyl-amine obtained in this way is dissolved in 733 ml of acetone and 11.2 g (0.63 mol) of water are added. 67.8 g (0.63 mol) of trimethylchlorosilane are slowly added. The reaction mixture is stirred at 5-8° C. for 72 hours. The solid which has precipitated out is then filtered off with suction and rinsed with acetone. The product is dried in a drying cabinet under 80-120 mbar at 45-50° C. for 16 hours. The yield is 134.4 g (58%) with a purity of 100.0%. The ratio of Z to E isomer is 99.05:0.95.

B) Hydrogenations (preparation of the two diastereomers (2R,3R)-[3-(3-methoxy-phenyl)-2-methyl-pentyl]-dimethyl-amine and (2R,3S)-[3-(3-methoxy-phenyl)-2-methyl-pentyl]-dimethyl-amine)

EXAMPLE B1

General Process for the Catalytic Hydrogenation

An autoclave is filled with argon under an applied pressure of 10-12 bar and is discharged again. This operation is carried out four times. 0.5 g (2.14 mmol) of the (Z)-(2R)-[3-(3-methoxy-phenyl)-2-methyl-pent-3-enyl]-dimethyl-amine obtained according to Example A.2 and 5 ml of freshly distilled ethanol are now placed in a 10 ml Schlenk vessel with a magnetic stirrer and this is exposed six times to a sequence of application of a high vacuum and letting down with argon. The solution is cooled to 0° C. with the aid of an ice bath and 70 μl (1.07 mmol) of methanesulfonic acid are then cautiously added. [Rh(nbd)$_2$]BF$_4$ (3.2 mg; 0.0086 mmol) and (S)-Solphos (ligand A, 6.0 mg; 0.0090 mmol) are added to a further 10 ml Schlenk vessel placed under argon by the above process and are dissolved in 5 ml of ethanol. The two solutions are stirred at RT for 10 min and then transferred into the autoclave by means of cannulas and a gentle stream of argon. The autoclave is filled with hydrogen gas (10 bar, four times) and hydrogen gas is finally forced in under 10 bar. The temperature is kept at 25° C. and stirring is started. After a reaction time of 67.5 h, the pressure is let down to normal pressure. A clear solution is obtained. The product is concentrated to dryness by means of a rotary evaporator at a bath temperature of about 40° C. The purity is determined as 94.1% by means of GC and the diastereomeric ratio of (2R,3R) to (2R,3S) or, respectively, trans:cis ratio is determined as 91.7:8.3 or, respectively, 11.1:1.

EXAMPLE B2

The results of Example B1 and further experiments carried out analogously to the process according to Example B1 are summarized in the following Table 1.

TABLE 1

| Catalyst/ligand | pH$_2$ [bar] | Time [h] | Conversion [%] | cis [%] | trans [%] |
|---|---|---|---|---|---|
| [Rh(nbd)$_2$] BF$_4$/(S)-A | 10 | 67.5 | 94.1 | 8.3 | 91.7 |
| [Rh(nbd)$_2$] BF$_4$/(S)-A | 20 | 16.5 | 37.0 | 10.4 | 89.6 |
| [Rh(nbd)$_2$] BF$_4$/(R)-A | 20 | 16.5 | 50.1 | 11.5 | 88.5 |
| [Rh(nbd)$_2$] BF$_4$/(R)-A | 20 | 67.5 | 77.8 | 12.5 | 87.5 |
| [Rh(nbd)$_2$] BF$_4$/(R)-(S)-B | 20 | 19.0 | 100 | 13.4 | 86.6 |
| [Rh(nbd)$_2$] BF$_4$/(R)-(S)-B | 20 | 20.0 | 97.6 | 18.5 | 81.5 |
| [Rh(nbd)$_2$] BF$_4$/(S)-(R)-B | 20 | 20.0 | 13.7 | 25.0 | 75.0 |
| [Rh(nbd)$_2$] BF$_4$/C | 20 | 20.0 | 41.5 | 14.5 | 85.5 |
| [Rh(nbd)$_2$] BF$_4$/C | 20 | 18.5 | 22.7 | 15.4 | 84.6 |
| [Rh(nbd)$_2$] BF$_4$/D | 20 | 20.0 | 4.0 | 16.7 | 83.3 |
| [Rh(nbd)$_2$] BF$_4$/E | 20 | 20.0 | 31.0 | 17.5 | 82.5 |
| [Rh(nbd)$_2$] BF$_4$/F | 20 | 20.0 | 6.2 | 21.4 | 78.6 |
| [Rh(nbd)$_2$] BF$_4$/(+)-G | 20 | 18.0 | 29.7 | 91.0 | 9.0 |
| [Rh(COD)$_2$] BF$_4$/(S)-(S)-H | 20 | 16.5 | 96.6 | 96.3 | 3.7 |
| [Rh(nbd)$_2$] BF$_4$/(S,S,S,S)-I | 20 | 19.0 | 100.0 | 75.2 | 24.8 |

Ligands: The structures of the ligands used are shown in the following:

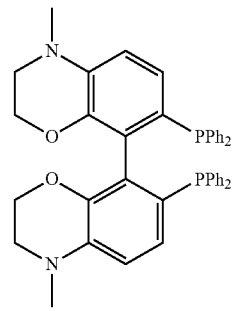

(A)

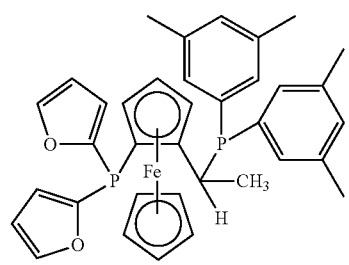

(B)

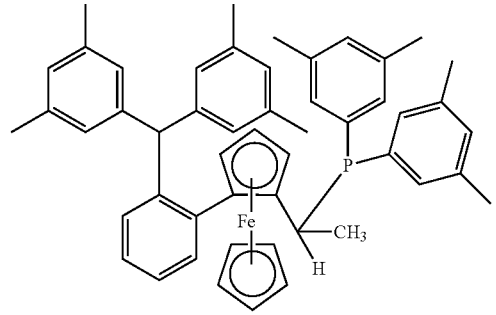

(C)

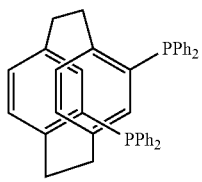 (D)

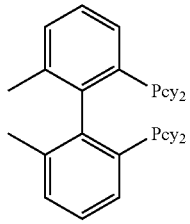 (E)

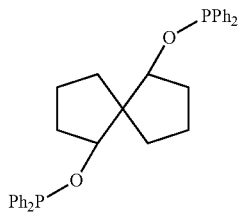 (F)

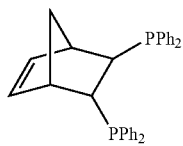 (G)

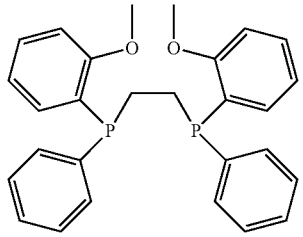 (H)

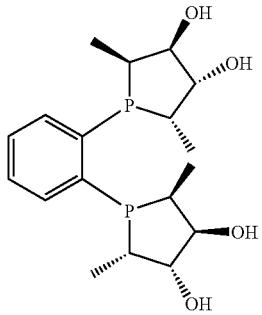 (I)

Note:

Only little is known of the hydrogenation of homo-allylic amines. Astonishingly, however, it is possible to prepare the two diastereomers (2R,3R)-[3-(3-methoxy-phenyl)-2-methyl-pentyl]-dimethyl-amine and (2R,3S)-[3-(3-methoxy-phenyl)-2-methyl-pentyl]-dimethyl-amine selectively in a high yield and optical purity with the homogeneous catalysis by varying the catalyst.

As a rule, the use of purified starting substance is advantageous for successful highly selective hydrogenation. For this, the mixture of (Z)-(2R)-[3-(3-methoxy-phenyl)-2-methyl-pent-3-enyl]-dimethyl-amine, (E)-(2R)-[3-(3-methoxy-phenyl)-2-methyl-pent-3-enyl]-dimethyl-amine and further unknown by-products which is obtained from the elimination is subjected to a hydrochloride precipitation.

In the case of hydrogenation of (Z)-(2R)-[3-(3-methoxy-phenyl)-2-methyl-pent-3-enyl]-dimethyl-amine with a homogeneous rhodium catalyst containing the ligand (S)-A, a purity of 94.1% and a diastereomeric ratio of the (2R,3R) to the (2R,3S) compound of 11.1:1 is achieved. Astonishingly, the hydrogenation with a rhodium catalyst which contains the other enantiomer of the ligand A, namely (R)-A, also give almost the same diastereomeric ratios as with the ligand (S)-A. It can therefore be assumed that a catalyst with the racemic ligand also produces good results, which is a considerable economic advantage.

If the ligand H is employed, the other diastereomer, the (2R,3S) compound is obtained with a purity of about 97% and a diastereomeric ratio of 29:1 (97%).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A process for preparing a substituted dimethyl-(3-aryl-butyl)amine compound corresponding to formula III:

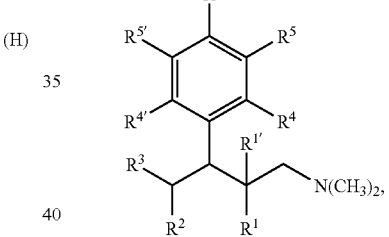

(III)

wherein
$R^1$, $R^{1'}$, $R^2$, $R^3$ each independently denote —H or —$C_{1-5}$-alkyl,
$R^4$, $R^{4'}$, $R^5$, $R^{5'}$, $R^6$ are identical or different and each represent —H, —OH, —$C_{1-4}$-alkyl, —O—$C_{1-4}$-alkyl, partly fluorinated or perfluorinated —$C_{1-4}$-alkyl, partly fluorinated or perfluorinated —O—$C_{1-4}$-alkyl, —O—$(CH_2)_n$-phenyl where n is 1, 2 or 3, F, Cl or $OR^8$, or two adjacent radicals $R^4$ and $R^5$, $R^5$ and $R^6$, $R^6$ and $R^{5'}$ or $R^{5'}$ and $R^{4'}$ represent a group —OCH=CHO—, —CH=C($R^9$)—O—, —CH=C($R^9$)—S— or —CH=CH—C($OR^{10}$)=CH— as part of a ring, with the proviso that the other particular radicals $R^6$, $R^5$ and $R^{4'}$, $R^4$, $R^{5'}$ and $R^{6'}$, $R^4$, $R^5$ and $R^{4'}$ or $R^4$, $R^5$ and $R^6$ have the abovementioned meaning,
$R^8$ denotes —CO—$C_{1-5}$-alkyl, —PO(O—$C_{1-4}$-alkyl)$_2$, —CO—$C_6H_4$—$R^{11}$, —CO(O—$C_{1-5}$-alkyl), —CO—CHR$^{12}$—NHR$^{13}$, —CO—NH—$C_6H_3$—$(R^{14})_2$ or an unsubstituted or substituted pyridyl, thienyl, thiazolyl or phenyl group,
$R^9$ denotes —H or —$C_{1-4}$-alkyl,
$R^{10}$denotes —H or —$C_{1-3}$-alkyl,
$R^{11}$denotes —OC(O)—$C_{1-3}$-alkyl in the ortho-position or —$CH_2$—N—$(R^{15})_2$ in the meta- or para-position, wherein $R^{15}$ in each case denotes —$C_{1-4}$-alkyl or the two radicals R^15 together with the bridging nitrogen atom form a 4-morpholino radical, R^12 and R^13 are identical or different and each represent —H, —C_{1-6}-alkyl or —C_{3-8}-cycloalkyl, or R^12 and R^13 together denote —(CH_2)_{3-8}— as part of a ring, and R^14 denotes —H, —OH, —C_{1-7}-alkyl, partly fluorinated or perfluorinated —C_{1-7}-alkyl, —OC_{1-7}-alkyl, -phenyl, —O-aryl, —F or —Cl, with the proviso that R^14 may be identical or different, said process comprising:
(a) choosing a homogeneous catalyst comprising a soluble rhodium salt or rhodium complex including an appropriate chiral diphosphine ligand with two secondary phosphine groups to prepare a specific diastereomer of a compound of formula III in a ratio of greater than or equal to 70:30 in favor of the specific diastereomer; and
(b) reacting a substituted dimethyl-(3-arylbut-3-enyl) amine compound corresponding to formula II:

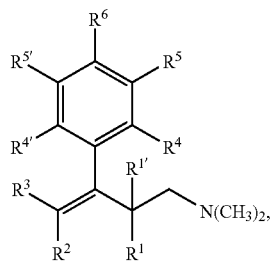

(II)

or a salt thereof,
wherein
R^1 and R^3 are methyl,
R^{1'} and R^2 are H,
R^4, R^{4'}, R^{5'}, and R^6 are H, and
R^5 is OCH_3,
in the presence of hydrogen and the homogeneous catalyst having the appropriate chiral diphosphine ligand,
wherein the chiral diphosphine ligands is:

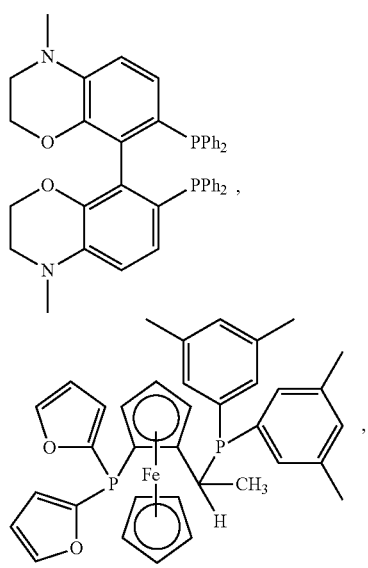

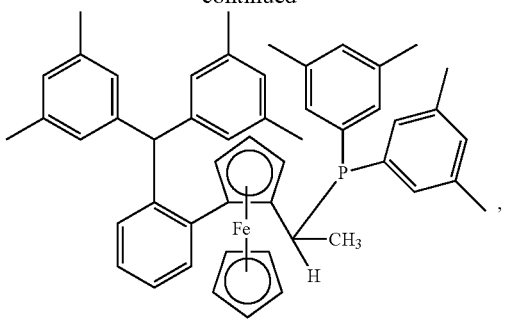

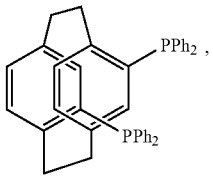

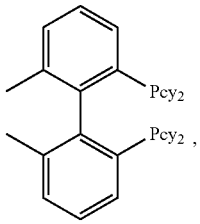

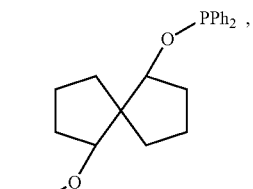

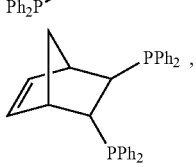

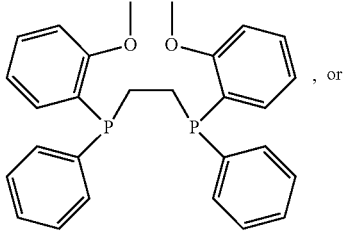, or

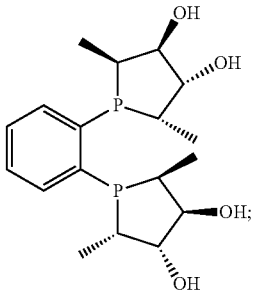

to prepare the specific diastereomer of the compound of formula III in the ratio of greater than or equal to 70:30 in favor of the specific diastereomer.

2. The process according to claim 1, wherein said compound of formula II is an isolated stereoisomer or an isolated E- or Z-isomer.

3. The process according to claim 1, wherein said compound of formula II is a mixture of stereoisomers or a mixture of E- or Z-isomers in any mixing ratio.

4. The process according to claim 1, wherein said compound of formula II is a racemic mixture.

5. The process according to claim 1, wherein the compound of formula II is (Z)-(2R)-3-[(3-methoxy-phenyl)-2-methyl-pent-3-enyl]-dimethylamine.

6. The process according to claim 5, wherein the specific diastereomer is (2R,3R)- or (2S,3R)-[3-(3-methoxy-phenyl)-2-methyl-pentyl]-dimethyl-amine.

7. The process according to claim 1, wherein:

the chiral diphosphine ligand is

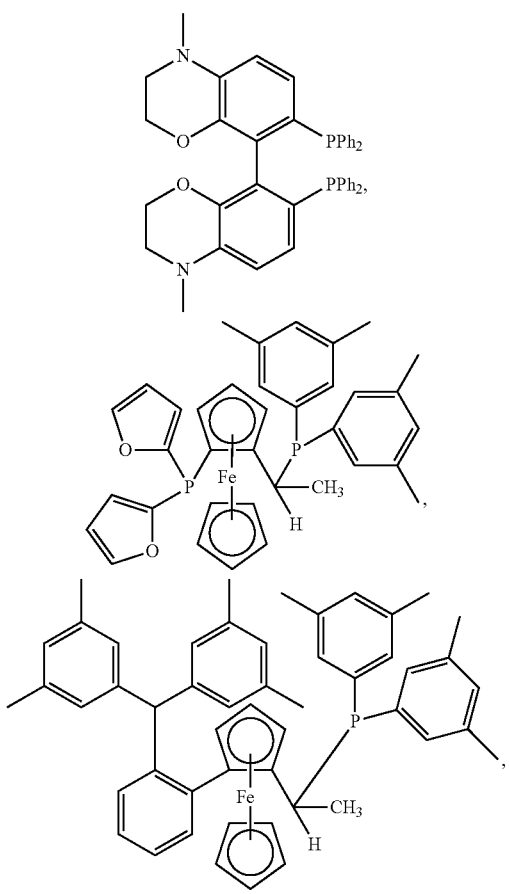

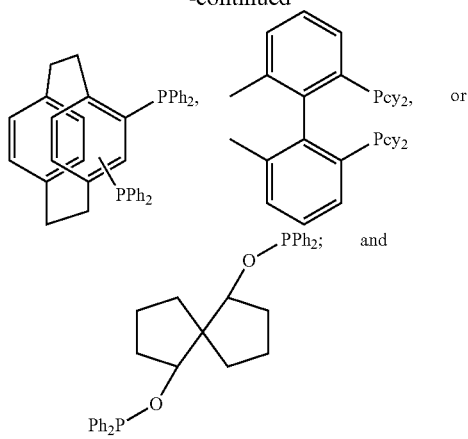

the specific diastereomer of the compound of formula III is the diastereomer (2R,3R)-[3-(3-methoxy-phenyl)-2-methyl-pentyl]-dimethyl-amine in a ratio (2R,3R):(2S,3R) of greater than or equal to 75:25.

8. The process according to claim 1, wherein the chiral diphosphine ligand is

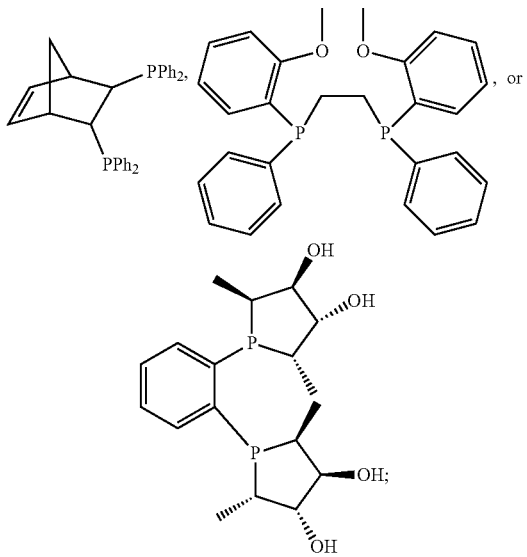

and the specific diastereomer of the compound of formula III is the diastereomer (2R,3S)-[3-(3-methoxy-phenyl)-2-methyl-penty]-dimethyl-amine in a ratio (2R,3S):(2R,3R) of greater than or equal to 75:25.

* * * * *

UNITED STATES PATENT AND TRADEMARK OFFICE
CERTIFICATE OF CORRECTION

| | | |
|---|---|---|
| PATENT NO. | : 8,791,300 B2 | Page 1 of 1 |
| APPLICATION NO. | : 12/113582 | |
| DATED | : July 29, 2014 | |
| INVENTOR(S) | : Hell et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 432 days.

Signed and Sealed this
Fifteenth Day of December, 2015

Michelle K. Lee
*Director of the United States Patent and Trademark Office*